US008735618B2

(12) United States Patent
Ludwig et al.

(10) Patent No.: US 8,735,618 B2
(45) Date of Patent: May 27, 2014

(54) SOLVENT-FREE ORGANOSILANE QUATERNARY AMMONIUM COMPOSITIONS, METHOD OF MAKING AND USE

(75) Inventors: Jerome H. Ludwig, Sun City West, AZ (US); Howard Ohlhausen, Paradise Valley, AZ (US)

(73) Assignee: Resource Development L.L.C., Scottsdale, AZ (US)

( * ) Notice: Subject to any disclaimer, the term of this patent is extended or adjusted under 35 U.S.C. 154(b) by 0 days.

(21) Appl. No.: 13/304,186

(22) Filed: Nov. 23, 2011

(65) Prior Publication Data
US 2012/0125226 A1 May 24, 2012

Related U.S. Application Data

(63) Continuation-in-part of application No. 12/775,799, filed on May 7, 2010, now abandoned.

(51) Int. Cl.
C07F 7/18 (2006.01)
C11D 1/62 (2006.01)
C11D 3/39 (2006.01)
C11D 3/00 (2006.01)

(52) U.S. Cl.
CPC ... *C07F 7/18* (2013.01); *C11D 1/62* (2013.01); *C11D 3/3947* (2013.01); *C11D 3/0036* (2013.01)
USPC ............... 556/413; 106/2; 106/504; 510/405; 510/369; 510/372

(58) Field of Classification Search
USPC ............... 556/413; 106/2, 504; 510/405, 369, 510/372, FOR. 161
See application file for complete search history.

(56) References Cited

U.S. PATENT DOCUMENTS

| 2,108,765 A | 2/1938 | Demagk |
| 2,612,458 A | 9/1952 | Stedman |
| 2,923,653 A | 2/1960 | Matlin et al. |
| 2,962,390 A | 11/1960 | Fain et al. |
| 3,130,164 A | 4/1964 | Best |
| 3,244,541 A | 4/1966 | Fain et al. |

(Continued)

FOREIGN PATENT DOCUMENTS

| AU | 493149 B2 | 5/1978 |
| CA | 1010782 | 5/1977 |

(Continued)

OTHER PUBLICATIONS

"Process aids for the Chemical Industry. Surfactants" Clariant International AG, (2008).*

(Continued)

*Primary Examiner* — David M Brunsman
(74) *Attorney, Agent, or Firm* — Wood, Herron & Evans, LLP

(57) ABSTRACT

Non-flammable, VOC-free organosilane quaternary ammonium compositions are provided in the form of pure or substantially pure water-soluble products that have bactericidal, fungicidal and viricidal activity and which are capable of bonding to various surfaces to form durable hydrophobic coatings. The resulting compositions are free of unreacted chloropropyltrialkoxysilanes, alkylamines and organic solvents that would otherwise provide flammable, corrosive, and/or toxic properties thereby inhibiting their safe and effective use in surface care, personal care and coating products.

25 Claims, No Drawings

(56) References Cited

U.S. PATENT DOCUMENTS

| | | | |
|---|---|---|---|
| 3,560,385 A * | 2/1971 | Ruth | 508/204 |
| 3,579,540 A | 5/1971 | Ohlhausen | |
| 3,580,385 A | 5/1971 | Thompson | |
| 3,730,701 A | 5/1973 | Isquith et al. | |
| 3,794,736 A | 2/1974 | Abbott et al. | |
| 3,817,739 A | 6/1974 | Abbott et al. | |
| 3,860,707 A | 1/1975 | Wootton | |
| 3,860,709 A | 1/1975 | Abbott et al. | |
| 3,865,728 A | 2/1975 | Abbott et al. | |
| 3,954,974 A | 5/1976 | Herzog et al. | |
| 4,005,025 A | 1/1977 | Kinstedt | |
| 4,005,028 A | 1/1977 | Heckert et al. | |
| 4,005,030 A | 1/1977 | Heckert et al. | |
| 4,161,518 A | 7/1979 | Wen et al. | |
| 4,259,103 A | 3/1981 | Malek et al. | |
| 4,282,366 A | 8/1981 | Eudy | |
| 4,311,598 A | 1/1982 | Verachtert | |
| 4,361,273 A | 11/1982 | Levine et al. | |
| 4,390,712 A | 6/1983 | Karl et al. | |
| 4,394,378 A * | 7/1983 | Klein | 514/63 |
| 4,397,757 A | 8/1983 | Bright et al. | |
| 4,406,892 A | 9/1983 | Eudy | |
| 4,421,796 A | 12/1983 | Burril et al. | |
| 4,430,236 A | 2/1984 | Franks | |
| 4,467,013 A | 8/1984 | Baldwin | |
| 4,557,854 A | 12/1985 | Plueddemann | |
| 4,567,039 A | 1/1986 | Stadnick et al. | |
| 4,576,728 A | 3/1986 | Stoddart | |
| 4,615,882 A | 10/1986 | Stockel | |
| 4,631,273 A | 12/1986 | Blehm et al. | |
| 4,682,992 A | 7/1987 | Fuchs | |
| 4,781,974 A | 11/1988 | Bouchette et al. | |
| 4,797,420 A | 1/1989 | Bryant | |
| 4,826,681 A | 5/1989 | Jacquet et al. | |
| 4,835,019 A | 5/1989 | White et al. | |
| 4,842,766 A | 6/1989 | Blehm et al. | |
| 4,847,088 A | 7/1989 | Blank | |
| 4,866,192 A | 9/1989 | Plueddemann et al. | |
| 4,908,355 A | 3/1990 | Gettings et al. | |
| 4,941,989 A | 7/1990 | Kramer et al. | |
| 4,990,377 A | 2/1991 | Wilson | |
| 4,999,249 A | 3/1991 | Deschler et al. | |
| 5,013,459 A | 5/1991 | Gettings et al. | |
| 5,209,775 A | 5/1993 | Bank et al. | |
| 5,281,357 A | 1/1994 | Morgan et al. | |
| 5,320,805 A | 6/1994 | Kramer et al. | |
| 5,348,556 A | 9/1994 | Minns et al. | |
| 5,360,568 A | 11/1994 | Madison et al. | |
| 5,360,569 A | 11/1994 | Madison et al. | |
| 5,411,585 A | 5/1995 | Avery et al. | |
| 5,426,204 A | 6/1995 | Harisiades et al. | |
| 5,478,357 A | 12/1995 | Madison et al. | |
| 5,552,476 A | 9/1996 | Halling | |
| 5,620,527 A | 4/1997 | Kramer et al. | |
| 5,736,582 A | 4/1998 | Devillez | |
| 5,798,144 A | 8/1998 | Varanasi et al. | |
| 5,885,951 A | 3/1999 | Loder | |
| 5,954,869 A | 9/1999 | Elfersy et al. | |
| 5,958,984 A | 9/1999 | Devillez | |
| 5,959,014 A | 9/1999 | Liebeskind et al. | |
| 6,060,552 A | 5/2000 | Kaido | |
| 6,087,319 A | 7/2000 | Norman | |
| 6,113,815 A | 9/2000 | Elfersy et al. | |
| 6,120,587 A | 9/2000 | Elfersy et al. | |
| 6,218,351 B1 | 4/2001 | Busch et al. | |
| 6,221,944 B1 | 4/2001 | Liebeskind et al. | |
| 6,240,929 B1 | 6/2001 | Richard et al. | |
| 6,307,425 B1 | 10/2001 | Chevallier et al. | |
| 6,309,425 B1 | 10/2001 | Murphy | |
| 6,310,230 B1 * | 10/2001 | Koski | 556/413 |
| 6,316,399 B1 | 11/2001 | Melikyan et al. | |
| 6,346,279 B1 | 2/2002 | Rochon | |
| 6,361,787 B1 | 3/2002 | Shaheen et al. | |
| 6,372,702 B1 | 4/2002 | Chiou et al. | |
| 6,376,448 B1 | 4/2002 | Colurciello, Jr. et al. | |
| 6,376,696 B1 * | 4/2002 | Raab et al. | 556/423 |
| 6,391,840 B1 | 5/2002 | Thompson et al. | |
| 6,403,547 B1 | 6/2002 | Grippaudo et al. | |
| 6,417,151 B1 | 7/2002 | Grothus et al. | |
| 6,432,181 B1 | 8/2002 | Ludwig | |
| 6,436,445 B1 | 8/2002 | Hei et al. | |
| 6,461,537 B1 | 10/2002 | Turcotte et al. | |
| 6,488,965 B1 | 12/2002 | Karageozian | |
| 6,528,472 B2 | 3/2003 | Charaf et al. | |
| 6,530,384 B1 | 3/2003 | Meyers et al. | |
| 6,534,075 B1 | 3/2003 | Hei et al. | |
| 6,548,467 B2 | 4/2003 | Baker et al. | |
| 6,559,111 B2 | 5/2003 | Colurciello, Jr. et al. | |
| 6,569,111 B2 | 5/2003 | Herzberg | |
| 6,610,777 B1 | 8/2003 | Anderson et al. | |
| 6,613,755 B2 | 9/2003 | Peterson et al. | |
| 6,676,733 B2 | 1/2004 | Ludwig et al. | |
| 6,740,626 B2 | 5/2004 | Neumiller | |
| 6,762,172 B1 | 7/2004 | Elfersy et al. | |
| 6,809,072 B2 | 10/2004 | Abidh et al. | |
| 6,881,247 B2 | 4/2005 | Batdorf | |
| 6,897,191 B2 | 5/2005 | Batdorf | |
| 6,921,576 B2 | 7/2005 | Terauchi et al. | |
| 6,994,890 B2 | 2/2006 | Ohlhausen et al. | |
| 7,151,139 B2 | 12/2006 | Tiller et al. | |
| 7,183,434 B2 | 2/2007 | Baan et al. | |
| 7,589,054 B2 | 9/2009 | Ohlhausen et al. | |
| 2002/0111282 A1 | 8/2002 | Charaf et al. | |
| 2003/0091541 A1 | 5/2003 | Ikehara et al. | |
| 2003/0109396 A1 | 6/2003 | Murphy et al. | |
| 2004/0096260 A1 | 5/2004 | Rhoades | |
| 2005/0020474 A1 | 1/2005 | Baan et al. | |
| 2005/0089659 A1 | 4/2005 | Fregonese et al. | |
| 2005/0089695 A1 | 4/2005 | Moffat et al. | |
| 2005/0096250 A1 | 5/2005 | Ohlhausen et al. | |
| 2006/0110348 A1 | 5/2006 | Ohlhausen et al. | |
| 2007/0010419 A1 | 1/2007 | Ohlhausen et al. | |
| 2007/0227557 A1 | 10/2007 | Ohlhausen et al. | |

FOREIGN PATENT DOCUMENTS

| | | |
|---|---|---|
| CA | 1217004 | 1/1987 |
| DE | 19538629 | 4/1997 |
| EP | 0051823 A1 | 5/1982 |
| EP | 0129980 A2 | 1/1985 |
| EP | 1741773 A1 | 1/2007 |
| WO | 9619558 A1 | 6/1996 |
| WO | 98/52954 | 11/1998 |
| WO | 0054587 | 9/2000 |
| WO | 0054587 A1 | 9/2000 |
| WO | 0072850 | 12/2000 |
| WO | 0072850 A1 | 12/2000 |
| WO | 2005042657 | 5/2005 |
| WO | 2006086271 | 8/2006 |
| WO | 2007008239 | 1/2007 |

OTHER PUBLICATIONS

Radell et al., Occlusion of Organosilanes by Urea, Journal of the American Chemical Society, vol. 80, p. 2683-5 (1958).

PCT US2005035996 International Search Report and Written Opinion of the International Search Authority.

PCT US2004030778 International Search Report and Written Opinion of the International Search Authority.

PCT US2006043351 International Search Report and Written Opinion of the International Search Authority, mailed Jul. 27, 2007.

Inorganic Chemistry: An Advanced Textbook, Chapter 14, "The Oxygen Family", Hydrogen Peroxide, pp. 504-506 (1954).

Witucki, Gerald L.; A Silane Primer: Chemistry and Applications of Alkoxy Silanes; Dow Corning Corporation, Journal of Coatings Technology Reprint, presented on Oct. 21, 1992.

Reregistration Eligibility Decision for Trimethoxysilyl Quaternary Ammonium Chloride Compounds; including letter from Frank T. Sanders and Table of Contents, p. 3 of Reregistration Eligibility Decision; EPA 739-R-07-007, Case No. 3148, Sep. 25, 2007.

PAN Pesticides Database—Pesticide Products, ZTREX 72 antimicrobial MUP; http://pesticideinfo.org; Jul. 3, 2007. (4 pages.).

(56) References Cited

OTHER PUBLICATIONS

Material Safety Data Sheet for Q9-6346 Silane, Dow Corning Corporation, Jan. 1, 2002. (9 pages).
Material Safety Data Sheet for ZTREX 72 Antimicrobial Agent MUP, Piedmont Chemical Industries I, LLC, Apr. 28, 2006 (3 pages).
Material Safety Data Sheet, "Hydrogen Peroxide (20 to 40%)," FMC Incorporation, Jun. 2008, pp. 1-11.
Invitation to Pay Additional Fees for PCT/US2011/035538, International Searching Authority, mailed Aug. 16, 2011.
Response to Invitation to Pay Additional Fees, David J. Josephic, dated Sep. 16, 2011.

* cited by examiner

SOLVENT-FREE ORGANOSILANE QUATERNARY AMMONIUM COMPOSITIONS, METHOD OF MAKING AND USE

RELATED APPLICATION

This application is a continuation-in-part application of U.S. Ser. No. 12/775,799 filed May 7, 2010, entitled Solvent-Free Organosilane Quaternary Ammonium Compositions, Method Of Making And Use, the disclosure of which is hereby incorporated herein by reference in its entirety.

FIELD OF THE INVENTION

This invention relates to the manufacture of solvent-free, storage-stable organosilicon quaternary ammonium compositions ("organosilane quats", "silane quats" or "silylated quaternary ammonium compounds"), particularly amorphous silane quats, without the need for or use of high pressure vessels, high temperatures, solvents and catalysts. The resulting compounds are pure or substantially pure mixtures of organosilane quats, i.e., "100% active", solvent-free, storage-stable, non-flammable and essentially free of unreacted chloropropyltrialkoxysilanes and alkylamines. By the practice of this invention, organosilane quaternary ammonium compositions are provided in a more useful form for shipping, storage and handling of the concentrated, 100% active compounds for various end uses including the cleaning of hard and soft surfaces, skin care and multifunctional coating compositions with antimicrobial properties. The cleaning, skin care and coating compositions yield invisible, but extremely durable, water, soil and stain repellent barrier coatings with antimicrobial benefits when applied to siliceous, plastic, metal, textile and skin surfaces.

BACKGROUND OF THE INVENTION

The utility and commercial potential of quaternary ammonium compounds was recognized, for example, in U.S. Pat. No. 2,108,765 issued in 1938 to Gerhard Domagk. Subsequent research in the field further broadened the understanding, structure and utility of the antimicrobial properties of quaternary ammonium compounds in sanitizers and disinfectants for hands and surfaces. From the 1960s to the 1980s, Dow Corning Corporation, Midland, Mich., undertook the research and development of a new class of silylated quaternary ammonium compounds, which resulted in a series of U.S. patents including the following: U.S. Pat. No. 3,560,385, issued Feb. 2, 1971, discloses siliconized quaternary ammonium salts; U.S. Pat. No. 3,730,701, issued May 1, 1973, discloses the siliconized quaternary ammonium compounds as antimicrobial agents; U.S. Pat. No. 3,794,736, issued Feb. 26, 1974, and U.S. Pat. No. 3,860,709, issued Jan. 14, 1975, disclose siliconized quaternary ammonium compounds for sterilizing or disinfecting a variety of surfaces and instruments; U.S. Pat. No. 3,817,739, issued Jun. 18, 1974, discloses siliconized quaternary ammonium compounds used to inhibit algae; U.S. Pat. No. 3,865,728, issued Feb. 11, 1975, discloses siliconized quaternary ammonium compounds used to treat aquarium filters. These prior art organosilane quaternary ammonium compositions are mixtures of alkylamine starting materials, chloroalkoxysilanes, and solvents as defined by the formula:

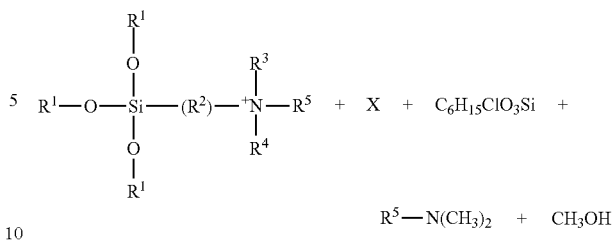

wherein $R^1$=hydrogen and/or $C_1$ to $C_4$ alkyl; $R^2$=divalent hydrocarbon radical with C1 to C8 carbon atoms; $R^3$=hydrogen or $C_1$ to $C_4$ alkyl; $R^4$=hydrogen or $C_1$ to $C_{10}$ alkyl; $R^5$=$C_8$ to $C_{22}$ saturated or unsaturated hydrocarbon radical and X=chloride (Cl—);
$C_6H_{15}ClO_3Si$=(3-chloropropyl)trimethoxysilane, $R^5$—N$(CH_3)_2$=alkylamines, and $CH_3OH$=methanol starting materials.

Prior art organosilane quaternary ammonium compounds are manufactured by reacting chloropropyltrialkoxysilanes, typically (3-chloropropyl)trimethoxysilane or (3-chloropropyl)triethoxysilane with mixtures of alkylamines, typically those that are predominantly octadecyldimethylamine, using alcoholic hydrocarbon solvents (methanol or ethanol) and various levels of heat and pressure, with or without catalysts, to enhance the speed and quality of the reaction.

Unless extensively fractionated and distilled, alkylamines are invariably mixtures of various derivatives of fatty acids (Table 2) that are converted to alkyl amines and further reacted with methyl chloride to form dimethylalkylamines; each component of which has a distinct molecular weight. Since chloropropyltrialkoxysilanes will react with each component of such amines, heretofore the commercial production of organosilane quaternary ammonium compositions actually yielded mixtures of organosilane quats. Such compositions are inherently unstable and are subject to hydrolysis, crosslinking and crystallization, with limited shelf lives.

Current commercial methodology yields organosilane quats that are only 42% or 72% active, with the balance being unreacted chloropropyltrialkoxysilanes, unreacted alkylamines and methanol. Also, these 42% or 72% active compounds are invariably flammable and/or toxic as manufactured and possibly as formulated into the ultimate end-use compositions. Their manufacturers invariably advise users that their products, even though containing 20% to 40% methanol, lack persistent storage stability and are subject to freeze/thaw degradation.

Commercially available organosilane quaternary ammonium compositions are offered by the following manufacturers, with activity levels and impurities (unreacted chloropropyltralkoxysilanes, unreacted alkylamines and solvents) as shown:
1. Dow Corning Q9-6346; Aegis AEM 5772; Piedmont Ztrex72; and Flexipel Q-1000—consisting of 72% by weight (3-trimethoxysilyl) dimethyloctadecyl ammonium chloride, 15% by weight (3-chloropropyl) trimethoxysilane, 13% by weight methyl alcohol and dimethyloctadecylamine at 1-5%.
2. Dow Corning 1-6136—consisting of 42% by weight (3-trimethoxysilyl) dimethyloctadecyl ammonium chloride, 8% by weight (3-chloropropyl) trimethoxysilane and 50% by weight methanol.

All of the above compositions contain (1) methanol, a solvent that is classified as flammable under D.O.T. Label Code Flammable Liquid and transportation Packaging Group II, and which is poisonous to humans; (2) chloropropyltrimethoxysilane that is toxic to humans and animals, ignitable and requires a Flammable Liquid N.O.S. label for domestic and ocean shipping and Hazard Class 3, Packing Group III, packaging for shipment by air; and (3) alkylamines that are present in unreacted form and which themselves can have toxicological, corrosive, and storage concerns as summarized in Table 1 below:

TABLE 1

PRINCIPAL HAZARDS OF METHANOL, ALKOXYSILANES AND ALKYLAMINES

| Hazard | Methanol | Alkoysilanes | Alkylamines |
| --- | --- | --- | --- |
| Flammable | Yes | Yes | No |
| Flash Point | 54° F. | 52° F. | >150° C. |
| Eye Irritant | Yes | Yes | Yes |
| Skin Irritant | Yes | Yes | Yes |
| Avoid Inhalation | Yes | Yes | Yes |
| Avoid Ingestion | Yes | Yes | Yes |
| Poison | Yes | Yes | Yes |
| Genetically Active | Yes | Yes | Yes |
| Marine Pollutant | Yes | Yes | Yes |
| Reactive to Acids | No | Yes | Yes |
| Reactive to Bases | No | Yes | No |

Even though these organosilane quaternary ammonium compositions are generally employed in end-use formulated compositions only to the extent of 0.1 to 1.0% of the active silane quat, the presence of flammable, poisonous solvents and unreacted silanes and amines can pose hazards and undermine their shipping, storage, handling and formulation into various end-use compositions.

Methods of making organosilane quaternary ammonium compounds have been described in the patent literature, for example, in U.S. Pat. No. 3,560,385, examples 1-5 disclose the reaction of alkylamines in solvent media at elevated temperatures employing excess chloropropyltrimethoxysilane resulting in compositions equivalent to the above described commercial products with 42%-72% activity levels with unreacted starting materials and solvents. U.S. Pat. No. 3,730, 701, Col. 2, lines 44-55, describes the general preparative procedure to make the C11-C22 silyl quaternary amine compounds in which a suitable solvent at ambient pressure is simply warmed with an appropriate tertiary amine and an appropriate silane. Alkylation of the tertiary amine with the alkyl halide occurs and the silyl quaternary amine compound is readily obtained. Col. 2, lines 59-68 acknowledges that the tertiary amines involved may be mixtures of long chain amines derived from natural products such as tallow, fish oils, coconut oil, etc., resulting in mixtures of silylated quaternary alkyl amines. U.S. Pat. No. 3,865,728 also discloses different amine mixtures (Col. 5, line 26 and 62) but does not specify or comment on the stoichiometry involved in the preparation of such compounds. U.S. Pat. No. 4,282,366, in Col. 3, lines 1-16, cites the Dow Corning U.S. Pat. Nos. 3,560,385 and 3,730,701 for making the silylated quaternary ammonium compounds in the conventional manner by heating the reactants at reflux temperatures in a polar solvent such as methanol, ethanol or acetone without reference to the purity or stoichiometry of the reactants. U.S. Pat. No. 4,394,378, in examples 1-2, discloses the reaction of didecylmethylamine with chloropropyltrimethoxysilane to produce organosilane quats containing unreacted silanes and solvent.

In summary, after more than 40 years, the prior art manufacturing process for making organosilane quats has remained the same. This is somewhat confirmed by the report by Donghuya University, Shanghai, Peoples Republic of China, and published in CA SELECTS, Volume 2009, Issue 23, Nov. 16, 2009. As reported, current methodology still involves the ongoing use of an excess of chloropropyltrialkoxysilanes for reaction with mixtures of alkylamines thereby resulting in organosilane quats containing unreacted starting materials and solvent. The ongoing practice of using excess starting materials (reactants) in solvents is further confirmed by a report from the College of Chemistry and Chemical Engineering, Shaanxi University of Science & Technology, Xi'an, Peoples Republic of China, and published in CA SELECTS, Volume 2010, Issue 7, Apr. 5, 2010. As reported therein, the optimal reaction for the synthesis of N, N-dimethyl-N-dodecylaminopropyltrimethoxy ammonium chloride was achieved by using the reaction medium dimethyl sulfoxide (DMSO) and a molar ratio excess of 10% of N, N-dimethyl-dodecylamine to y-chloropropyltrimethoxy silane at 120° C.

Still today, manufacturers are offering organosilane quats in concentrations of 40-72% in methanol and other solvents, which are flammable, toxic, and poisonous. Moreover, as such concentrated quats age, their viscosities, appearance, color, and compounding ability vary significantly.

The need for storage-stable, nonflammable forms of organosilane quats has been addressed most recently in U.S. Pat. No. 7,589,054, which discloses new clathrate forms of the organosilane quats which are storage-stable solids. The solid clathrates provide a new storage-stable, nonflammable, and nontoxic form of the organosilane quat. These urea-organosilane quat clathrates solve a number of problems presently confronting the use of otherwise highly-reactive quats. A clathrate form of the urea-organosilane quats overcomes the problems of lack of storage stability, handling, and shipping hazards associated with the existing 40-72% concentrations in methanol or other solvents. Nevertheless, there is still a need for new methods of making the organosilane quats so that they may be offered in a more acceptable form without the disadvantages and current problems associated with the 40-72% concentrations in methanol, as are now offered by current manufacturers.

SUMMARY OF THE INVENTION

In summary, this invention is directed to a more satisfactory solution to the above-discussed problems associated with the production and utilization of organosilane quats. This invention has as one of its principal objectives the preparation of a solvent-free, storage-stable composition comprising a mixture of organosilane quats which is substantially free of alkyl amines, solvent, and chloropropylsilanes. In another of its main aspects, this invention provides for an improved method for the production of organosilane quats which enables an essentially complete reaction of the starting materials without the need for catalysts, solvents, high pressure, or high temperature, as involved in current techniques. A further objective of this invention is to provide forms of organosilane quaternary ammonium compounds that are amorphous, nonflammable liquids or solids, in the form of crystals, oils and waxes, and which are infinitely storage stable, water and/or alcohol dilutable, substantially 100% active and capable of bonding to hard and soft surfaces.

Applicants have found that solvent-free, storage stable, amorphous silane quats can be manufactured by using a more precise equivalent weight ratio of reactants and without the need for high temperature reactions and/or solvents that are added to facilitate the reaction and/or to provide storage stability, The inventive method is predicated in part upon the need to first determine the molecular composition and equivalent weight of the mixture of alkyl amines and haloalkyltrialkoxysilane before conducting the reaction. In one form of the invention, hereinafter referred to as the "analytical technique", this is done by identifying each of the alkyl amines in the amine mixture and the relative percentages by weight of each of the amines, so that the equivalent weight of the entire amine mixture is determined. In another form of the invention, hereinafter referred to as the "nitrogen technique", the percentage by weight of nitrogen in the amine mixture is used to determine the equivalent weight of the entire amine mixture. This is done by dividing the percentage by weight of nitrogen by the molecular weight of nitrogen.

Using either the analytical technique or the nitrogen technique, the equivalent weight is determined as that quantity of the alkyl amine mixture that more precisely reacts with, or is equal to the combining value of, the haloalkyloxysilane in the reaction. The reaction of these equivalent weights produces a solvent-free, storage stable composition of organosilane quats that are essentially 100% active and substantially free of solvent and the alkylamine and organosilane starting materials.

Notwithstanding the decades of prior art methodology, it is not been reported that an essentially complete reaction of chloropropyltrialkoxysilanes and alkyl amines can be carried out to produce a substantially pure organosilane quaternary ammonium composition which is essentially 100% active. Such a composition can be effectively diluted with water or solvents to make ready-to-use compositions with activity levels as low as 0.0002% (500 ppm) and with hydrophobic coating effectiveness, on various surfaces, that is superior to existing commercially available impure, solvent-containing compositions and without the need to remove the impurities (i.e., unreacted silanes, amines and solvents).

Accordingly, this invention offers a new approach and a satisfactory solution to the problems associated with the manufacture and utilization of organosilane quats. A further understanding of the invention, its various embodiments, and operating parameters will be apparent with reference to the following Detailed Description.

DETAILED DESCRIPTION OF THE INVENTION

In accordance with the above summary, the objectives of this invention are to provide solvent-free, storage-stable organosilane compositions and methods for manufacturing them in essentially 100% active form. The most preferred embodiments of this invention are hereinafter described without the need for catalysts, solvents, pressure vessels, or high temperatures.

A. Solvent-Free, Storage-Stable Compositions

The solvent-free, storage-stable compositions of this invention comprise a mixture of organosilane quaternary ammonium compounds defined by the formula:

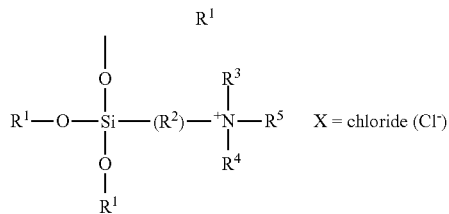

wherein $R^1$=hydrogen and/or $C_1$ to $C_4$ alkyl; $R^2$=divalent hydrocarbon radical with $C_1$ to $C_8$ carbon atoms; $R^3$=hydrogen or $C_1$ to $C_4$ alkyl; $R^4$=hydrogen or $C_1$ to $C_{10}$ alkyl; $R^5$=$C_8$ to $C_{22}$ saturated or unsaturated hydrocarbon radical and X=chloride ions, said composition substantially free of alkyl amines, solvent and chloroalkylsilanes.

In compositions according to the above formula, $R^1$ is methyl or ethyl, $R^2$ is propyl, $R^3$ is methyl, $R^4$ is methyl or hydrogen, and $R^5$ is octyl, decyl, dodecyl, tetradecyl, tetradecenyl, hexadecyl, palmitoleyl octadecyl, oleyl, linoleyl, docosyl, or icosyl. Specific examples of the organosilane quaternary ammonium compounds and mixtures thereof are selected from the group consisting of:

3-(trimethoxysilyl)propyldimethyloctadecyl ammonium chloride,
 3-(trimethoxysilyl)propyldimethyldecyl ammonium chloride,
 3-(trimethoxysilyl)propyldimethyldodecyl ammonium chloride,
 3-(trimethoxysilyl)propyldidecylmethyl ammonium chloride,
 3-(trimethoxysilyl)propyltetradecyldimethyl ammonium chloride,
 3-(trimethoxysilyl)propyldimethylhexadecyl ammonium chloride,
 3-(trimethoxysilyl)propyldimethylsoya ammonium chloride,
 3-(trimethoxysilyl)propyldimethyloleyl ammonium chloride,
 3-(trimethoxysilyl)propyldimethylpalmitoleyl ammonium chloride,
 3-(trimethoxysilyl)propyldimethylicosyl ammonium chloride,
 3-(trihydroxysilyl)propyldimethyloctadecyl ammonium chloride,
 3-(trimethoxysilyl)propyloctyl ammonium chloride,
 3-(trimethoxysilyl)propyldecyl ammonium chloride,
 3-(trimethoxysilyl)propyltetradecyl ammonium chloride,
 3-(trimethoxysilyl)propyltetradecenyl ammonium chloride,
 3-(trimethoxysilyl)propylhexadecyl ammonium chloride,
 3-(trimethoxysilyl)propylpalmitoleyl ammonium chloride,
 3-(trimethoxysilyl)propyloctadecyl ammonium chloride,
 3-(trimethoxysilyl)propyloleyl ammonium chloride,
 3-(trimethoxysilyl)propyldocosyl ammonium chloride,
 3-(trimethoxysilyl)propylicosyl ammonium chloride,
 3-(trimethoxysilyl)propyldimethylmyristoleyl ammonium chloride, and
 3-(trimethoxysilyl)propyldimethyldocosyl ammonium chloride, and mixtures thereof.

Storage-stable cleansing and multifunctional coating compositions for treating a surface, thereby rendering it water and soil repellent, may be formulated as liquid end-use products. When formulated into end-use products, the organosilane quat mixtures are employed with a diluent, preferably water, in concentrations on the order of at least about 0.0002% by weight of the organosilane quats in the diluent based upon the total weight of the quats and diluent. The end-use products may be in the form of a liquid, slurry, cream, or powder. Moreover, concentrates and intermediates, for dilution into end-use products, may be formed wherein the organosilane quat is present in an amount of about 1% or more by weight. Also, end-use products may contain nonreactive abrasive solids in an amount up to 35% by weight. The abrasive solids are selected from a group consisting of coated and uncoated urea, silicas, silicates, metal oxides, metal carbonates, clays, carbides, and plastics. Storage stable additives may also be included in the compositions including those selected from the group consisting of surfactant, thickener, gelling agent, abrasive, lubricant, diluent, and solvents and mixtures thereof. Peroxides such as hydrogen peroxide or complexes thereof may also be added to the basic neat composition, and the peroxide is generally in an amount up to about 8% by weight, or normally up to 3% by weight, with organosilane quats up to about 3% by weight. Accordingly, the compositions may be formulated within the scope of this invention to provide cleansing and multifunctional coating compositions for bonding onto a surface, thereby rendering it (a) water and soil repellent, (b) antimicrobial, and (c) for easier next-time cleaning as disclosed in the Ohlhausen and Ludwig U.S. Pat. No. 6,994,890, filed Oct. 31, 2003, U.S. Pat. No. 7,704,313, filed Jul. 6, 2005, and U.S. Pat. No. 7,754,004, filed May 25, 2007, which are incorporated herein by reference.

B. Methods of Making the Storage-Stable Mixture of Organosilane Quats

This invention is predicated in part upon the discovery of a new method for making organosilane quats from a mixture of alkyl amines and haloalkyltrialkoxysilanes. This method involves first determining the molecular composition and equivalent weight of the mixture of alkyl amines and the chloroalkyltrialkoxysilane. This is a critical step in the method and, heretofore, has not been reported in the prior art.

Two techniques have been found to satisfy this first critical step, as referred to above:

B1—Analytical Technique

The molecular composition and equivalent weight of the amine mixture is determined by identifying (measuring) the relative percentage by weight of each amine in the mixture to determine the equivalent of the entire mixture.

B2—Nitrogen Technique

The molecular composition and equivalent weight of the amine mixture is determined by identifying (measuring) the percentage by weight of nitrogen in the mixture to determine the equivalent weight of the entire mixture.

Then, at a ratio of 1:1, the equivalent weight of said alkyl amine mixture with the equivalent weight of the haloalkyltrialkoxysilane is reacted to form a storage-stable composition of the mixture of organosilane quaternary ammonium compounds defined by the formula:

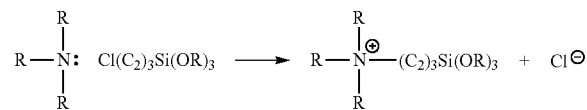

wherein $R^1$=hydrogen and/or $C_1$ to $C_4$ alkyl; $R^2$=divalent hydrocarbon radical with $C_1$ to $C_8$ carbon atoms; $R^3$=hydrogen or $C_1$ to $C_4$ alkyl; $R^4$=hydrogen or $C_1$ to $C_{10}$ alkyl; $R^5$=$C_8$ to $C_{22}$ saturated or unsaturated hydrocarbon radical and X=chloride, said composition substantially free of alkyl amines, solvent and chloroalkylsilanes.

In accordance with the above method, the haloalkyltrialkoxysilane is selected from the group consisting of a chloro-lower alkyl $C_1$ to $C_8$ trialkoxysilane, more preferably selected from the group consisting of chloropropyltrimethoxysilane and chloropropyltriethoxysilane. The alkyl amines may be primary, secondary, or tertiary alkyl amines. Examples of amines include:

octyldimethyl amine,
decyldimethyl amine,
dodecyldimethyl amine,
tetradecyldimethyl amine,
hexadecyldimethyl amine,
octadecyldimethyl amine,
palmitoleyldimethyl amine,
oleyldimethyl amine,
icosyldimethyl amine,
myristoleyldimethyl amine,
dodecyl amine,
tetradecyl amine,
myristoleyl amine,
hexadecyl amine,
palmitoleyl amine,
octadecyl amine,
oleyl amine,
icosyl amine,
docosyl amine,
octyl amine, and
decyl amine, and mixtures thereof.

In a preferred form, the method is practiced without the need for catalysts, solvents, pressure vessels, or high temperatures. The temperatures normally employed are on the order of about 20° C. to about 120° C.

The method will be further understood with reference to the stoichiometry of the reaction between the alkyl amines and chloropropyltrialkoxysilanes as shown by the following equation:

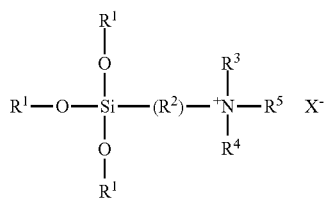

The chloropropyltrialkoxysilanes most typically employed are (3-chloropropyl)trimethoxysilane and (3-chloropropyl)triethoxysilane, and are distilled compounds commercially available from various manufacturers of silicones such as Dow-Corning Corporation as Z-6076 and Z-6376, and from Shin-Etsu Silicones as KBM 703 KBM 903, respectively as follows.

Chloropropyltrimethoxysilane:
  Equivalent Weight: 198.72
  Formula: $C_6H_{15}ClO_3Si$
  Composition: C 36.3% H 7.6% O 24.2% Cl 17.8% Si 14.1%

Chloropropyltriethoxysilane:
  Equivalent Weight: 240.80
  Formula: $C_9H_{21}ClO_3Si$
  Composition: C 44.9% H 8.8% O 19.9% Cl 14.7% Si 11.7%

The alkylamines are usually based on the nature and source of the fatty acid employed in the amine synthesis as follows:

TABLE 2

Chain Length Distribution of Raw Materials Used for Alkyl Amines

| Acid Name | Coco | Palm | Tallow | Hard Tallow | Soya |
|---|---|---|---|---|---|
| Caproic | 0.5 | | | | |
| Caprylic | 7 | | | | |
| Capric | 6 | | | | |
| Lauric | 48 | | | | |
| Myristic | 19 | 2 | 3.5 | 4.5 | |
| Myristoleic | | | 1 | | |

TABLE 2-continued

Chain Length Distribution of Raw Materials Used for Alkyl Amines

| Acid Name | Coco | Palm | Tallow | Hard Tallow | Soya |
|---|---|---|---|---|---|
| Pentadecanoic | | | 0.5 | 0.5 | |
| Palmitic | 9 | 42 | 25.3 | 29.3 | 11 |
| Palmitoleic | | | 4 | | |
| Margaric | | | 2.5 | 2.5 | |
| Stearic | 3 | 4 | 19.4 | 52.7 | 4 |
| Oleic | 6 | 43 | 40.8 | | 21 |
| Linoleic | 1.5 | 9 | 2.5 | | 55.5 |
| Linolenic | | | | | 8.5 |
| Arachidic | | | 0.5 | 0.5 | |
| Typical Iodine Value | 10 | 50 | 45 | 3 | 140 |

The alkylamines produced from the foregoing natural fatty acids are further reacted with methyl chloride to provide alkylamines, for example the dimethylalkylamines, used most frequently for the production of the organosilane quaternary ammonium compositions. A broad range of alkylamines is commercially available from manufacturers such as Akzo Nobel, Albemarle Corporation and Corsicana, as mixtures of distilled aliphatic (fatty) amines with varying carbon chain lengths as shown in Table 3, Column 1.

TABLE 3

| Product/Composition | Column 1 % Weight | Column 2 Mol. Wt. | Column 3 Moles | Column 4 Equiv. Wt. 1 Mole |
|---|---|---|---|---|
| ADMA 8* | | | | |
| Octyldimethyl amine | 99.53% | 157.30 | 0.632740 | |
| Decyldimethyl amine | 0.47% | 185.35 | 0.002536 | |
| | 100.00% | | 0.635276 | 157.412 |
| ADMA 10* | | | | |
| Octyldimethyl amine | 0.08% | 157.30 | 0.000509 | |
| Decyldimethyl amine | 99.61% | 185.35 | 0.537416 | |
| Dodecyldimethyl amine | 0.31% | 213.40 | 0.001453 | |
| | 100.00% | | 0.539378 | 185.399 |
| ADMA 12* | | | | |
| Decyldimethyl amine | 0.23% | 185.35 | 0.001241 | |
| Dodecyldimethyl amine | 98.94% | 213.40 | 0.463636 | |
| Tetradecyldimethyl amine | 0.83% | 241.46 | 0.003437 | |
| | 100.00% | | 0.468314 | 213.532 |
| ADMA 14* | | | | |
| Dodecyldimethyl amine | 0.64% | 213.40 | 0.002999 | |
| Tetradecyldimethyl amine | 99.03% | 241.46 | 0.410130 | |
| Hexadecyldimethyl amine | 0.31% | 269.51 | 0.001150 | |
| Octadecyldimethyl amine | 0.01% | 297.56 | 0.000034 | |
| | 100.00% | | 0.414313 | 241.363 |
| ADMA 16* | | | | |
| Dodecyldimethyl amine | 0.06% | 213.40 | 0.000281 | |
| Tetradecyldimethyl amine | 0.67% | 241.46 | 0.002775 | |
| Hexadecyldimethyl amine | 98.55% | 269.51 | 0.365664 | |
| Octadecyldimethyl amine | 0.72% | 297.56 | 0.002420 | |
| | 100.00% | | 0.371114 | 269.459 |
| ADMA 18* | | | | |
| Dodecyldimethyl amine | 0.10% | 213.40 | 0.000469 | |
| Hexadecyldimethyl amine | 1.40% | 269.51 | 0.005195 | |
| Octadecyldimethyl amine | 98.50% | 297.56 | 0.331026 | |
| | 100.00% | | 0.336690 | 297.009 |
| Armeen DMHTD** | | | | |
| Tetradecyldimethyl amine | 4.00% | 241.46 | 0.016566 | |
| Hexadecyldimethyl amine | 32.90% | 269.51 | 0.122073 | |
| Polmitoleyldimethyl amine | 0.30% | 267.49 | 0.001122 | |

TABLE 3-continued

| Product/Composition | Column 1 % Weight | Column 2 Mol. Wt. | Column 3 Moles | Column 4 Equiv. Wt. 1 Mole |
|---|---|---|---|---|
| Octadecyldimethyl amine | 59.80% | 297.55 | 0.200968 | |
| Oleyldimethyl amine | 2.50% | 295.53 | 0.008459 | |
| Linoleyldimethyl amine | 0.20% | 293.52 | 0.000681 | |
| Icosyldimethyl amine | 0.30% | 325.62 | 0.000921 | |
| | 100.00% | | 0.350790 | 285.071 |
| Armeen DMOD** | | | | |
| Dodecyldimethyl amine | 0.50% | 213.4 | 0.002343 | |
| Tetradecyldimethyl amine | 1.50% | 241.46 | 0.006212 | |
| Myristoleyldimethyl amine | 0.50% | 239.44 | 0.002088 | |
| Hexadecyldimethyl amine | 4.00% | 269.51 | 0.014842 | |
| Polmitoleyldimethyl amine | 4.00% | 267.49 | 0.014954 | |
| Octadecyldimethyl amine | 14.10% | 297.55 | 0.047385 | |
| Oleyldimethyl amine | 70.40% | 295.53 | 0.238200 | |
| Linoleyldimethyl amine | 5.00% | 293.52 | 0.017034 | |
| | 100.00% | | 0.343058 | 291.496 |
| Armeen OD** | | | | |
| Dodecyl amine | 0.50% | 185.35 | 0.002698 | |
| Tetradecyl amine | 1.50% | 231.40 | 0.006482 | |
| Myristoleyl amine | 0.50% | 211.39 | 0.002365 | |
| Hexadecyl amine | 4.00% | 241.46 | 0.016566 | |
| Polmitoleyl amine | 4.00% | 239.44 | 0.016706 | |
| Octadecyl amine | 14.10% | 269.51 | 0.052317 | |
| Oleyl amine | 71.40% | 267.49 | 0.266926 | |
| Linoleyl amine | 5.00% | 265.48 | 0.018835 | |
| | 100.00% | | 0.382894 | 261.169 |
| Armeen 18D** | | | | |
| Hexadecyl amine | 2.50% | 241.46 | 0.010354 | |
| Octadecyl amine | 96.60% | 267.49 | 0.358428 | |
| Oleyl amine | 0.50% | 263.76 | 0.001896 | |
| Icosyl amine | 0.40% | 297.56 | 0.001344 | |
| | 100.00% | | 0.372022 | 268.801 |
| Armeen CD** | | | | |
| Octyl amine | 5.00% | 129.24 | 0.038688 | |
| Decyl amine | 6.00% | 157.30 | 0.038144 | |
| Dodecyl amine | 50.00% | 185.35 | 0.269760 | |
| Tetradecyl amine | 19.00% | 213.40 | 0.089035 | |
| Hexadecyl amine | 10.00% | 241.46 | 0.041415 | |
| Octadecyl amine | 10.00% | 269.51 | 0.037104 | |
| | 100.00% | | 0.514146 | 194.497 |

Manufactured by
*ALBEMARLE Amines
**AKZO NOBEL Amines

C. Operating Examples 1-13 (Analytical Technique)

With reference to Operating Examples 1-13 of Tables 4 and 5, the 1:1 molar ratios or equivalent weights of various alkylamine mixtures and chloropropyltrialkoxysilanes as shown were determined using Table 3, as follows. The weight percent of the amine mixtures in Table 3, Column 1, were provided by the manufacturers of particular amine mixtures. Table 3, Column 2 shows the molecular weight of each amine component as determined from its chemical formula. To determine the number of moles of each amine component in the mixture, its percent weight (in grams) was divided by its molecular weight; with the results shown in Table 3, Column 3. The number of moles of each component of the amine mixture were added, and that sum was divided into 100 (grams) to determine the equivalent weight of 1 mole of the amine mixture as shown in Table 3, Column 4. The equivalent weight of chloropropyltrialkoxysilane(s) was determined in the same fashion. To react a specific quantity of an amine mixture with a chloropropyltrialkoxysilane on a 1:1 equivalent weight basis, the amount of amine mixture—in grams—determines the moles of chloropropyltrialkoxysilane required for the reaction, or vice versa as shown in Tables 4 and 5. The reactants were weighed and mixed in glass reaction vessels of varying sizes and capacities such as Erlenmeyer flasks with appropriate stoppers. The vessels were then placed in an air circulation oven and heated to temperatures between 90° C. to 100° C. for the time periods shown in Tables 3 and 4. At approximately 16 hour intervals while heating, the mixtures were assayed for the percent of reaction completion, until 100% was achieved.

TABLE 4

EXAMPLES (ANALYTICAL TECHNIQUE)
1:1 EQUIVALENT WEIGHT REACTIONS

| | EXAMPLE No. | | | | | | |
|---|---|---|---|---|---|---|---|
| | 1 | 2 | 3 | 4 | 5 | 6 | 7 |
| Amine | ADMA 18 | ADMA 16 | ADMA 14 | ADMA 12 | ADMA 10 | DMOD | OD |
| Equivalent Weight | 297.009 | 269.459 | 241.363 | 213.532 | 185.399 | 291.496 | 261.169 |
| Grams | 194.37 | 100.00 | 100.00 | 99.99 | 100.00 | 306.09 | 150.53 |
| Moles | 0.6544 | 0.37111 | 0.41431 | 0.4863 | 0.53938 | 1.05007 | 0.5664 |
| Chloropropyltrialkoxysilane | KBM 703 | KBM 703 | KBM 703 | KBM 703 | KBM 703 | KBM 703 | KBM 703 |
| Equivalent Weight | 198.72 | 198.72 | 198.72 | 198.72 | 198.72 | 198.72 | 198.72 |
| Grams | 130.04 | 73.747 | 82.33 | 96.637 | 107.19 | 208.667 | 114.54 |
| Available Chlorine Atoms - Wgt. % | 23.15 | 13.13 | 14.65 | 17.20 | 19.08 | 37.14 | 20.39 |
| Mole(s) | 0.6544 | 0.37111 | 0.41418 | 0.4863 | 0.53938 | 1.05007 | 0.5764 |
| Reaction Temp. (° C.) | 95° | 90° | 90° | 90° | 90° | 98° | 100° |
| Reaction Time (Hrs) | 47 | 107 | 107 | 67 | 107 | 101 | 88 |
| Reacted Product Assay | | | | | | | |
| Titration (ppm) | 500 | 500 | 500 | 500 | 500 | 500 | 500 |
| % Complete | 100% | 100% | 100% | 100% | 100% | 100% | 100% |
| pH Hydrion Quat Chek (ppm) | 400-600 | 400-600 | 400-600 | 400-600 | 400-600 | 400-600 | 400-600 |
| Free Chloride Ions - Wgt. % (Calculated) | 7.14 | 7.56 | 8.03 | 8.75 | 9.21 | 7.22 | 7.69 |
| Form | Hard Wax | Soft Wax | Soft Wax | Oil | Oil | Oil | Soft Wax |
| Non-Crystalline | Yes | Yes | Yes | Yes | Yes | Yes | Yes |
| Product Performance | | | | | | | |
| Aqueous solution @ 500 ppm | Clear | Clear | Clear | Clear | Clear | Clear | Clear |
| Barrier coating on glass surface | yes | yes | yes | yes | yes | yes | yes |
| Coated glass repels ink highlighter | yes | yes | yes | yes | yes | yes | yes |

TABLE 5

EXAMPLES (ANALYTICAL TECHNIQUE)
1:1 EQUIVALENT WEIGHT REACTIONS

| | EXAMPLE No. | | | | | |
|---|---|---|---|---|---|---|
| | 8 | 9 | 10 | 11 | 12 | 13 |
| Amine | Armeen 18D | Armeen CD | ADMA 18 | ADMA 16 | ADMA 14 | ARMEEN CD |
| Equivalent Weight | 268.801 | 194.497 | 297.009 | 269.459 | 241.339 | 194.487 |
| Grams | 150.00 | 150.00 | 75.00 | 150.00 | 75.00 | 50 |
| Mole(s) | 0.5580 | 0.7712 | 0.2525 | 0.5567 | 0.31077 | 0.2571 |
| Chloropropyltrialkoxysilane | KB 703 | KB 703 | Z-6376 | Z-6376 | Z-6376 | KBM 703 |
| Equivalent Weight | 198.72 | 198.72 | 240.80 | 240.80 | 240.80 | 198.72 |
| Grams | 110.9 | 153.25 | 60.800 | 134.05 | 74.8334 | 51.091 |
| Available Chlorine Atoms - Wgt. % | 19.74 | 27.28 | 8.93 | 19.71 | 11.001 | 9.09 |
| Mole(s) | 0.5580 | 0.7712 | 0.2525 | 0.5567 | 0.31077 | 0.2571 |
| Reaction Temp. (° C.) | 100° | 100° | 90° | 100° | 90° | 108° |
| Reaction Time (Hrs) | 88 | 85 | 140 | 81 | 140 | 32 |
| Reacted Product Assay | | | | | | |
| Titration (ppm) | 500 | 500 | 500 | 500 | 500 | 500 |
| % Complete | 100% | 100% | 100% | 100% | 100% | 100% |
| pH Hydrion Quat Chek (ppm) | 400-600 | 400-500 | 400-600 | 400-600 | 400-600 | 400-600 |
| Free Chloride Ions - Wgt. % (Calculated) | 7.57 | 8.99 | 6.58 | 6.94 | 7.34 | 8.99 |
| Form | Hard Wax | Hard Wax | Soft Wax | Cream | Cream | Hard Wax |
| Non-Crystalline | Yes | Yes | Yes | Yes | Yes | Yes |
| Product Performance | | | | | | |
| Aqueous solution @ 500 ppm | Slightly Cloudy | Clear | Clear | Clear | Clear | Clear |
| Barrier coating on glass surface | yes | yes | yes | yes | yes | yes |
| Coated glass repels ink highlighter | yes | yes | yes | yes | yes | yes |

D. Operating Examples 14-19 (Nitrogen Technique)

With reference to Operating Examples 14-19 of Table 7, the nitrogen technique was employed to conduct 1:1 equivalent weight reactions between the Product/Composition for the amine mixtures identified in Table 6 with the chloropropyltrialkoxy silane identified in Table 7. The Product/Composition of the amine mixtures is set forth in Column 1, and this information was provided by the manufacturers of the particular amine mixtures as identified in the footnotes of Table 6. Table 6, Column 2, shows the percent by weight of nitrogen in the Product/Composition amine mixture information. The percent by weight of nitrogen was determined by the classic Dumas method, with thermal conductivity detection (TCD) using a ThermoFlashEA 1112 analyzer. The method is described in ASTM D5291 (petroleum products). Weighed samples are combusted in oxygen at 950° C. The combustion products (including $N_2$ and NOx) are swept with a helium carrier gas through combustion catalysts, scrubbers, and through a tube filled with reduced copper. The copper removes excess oxygen and reduces NOx to $N_2$. The $N_2$ is then separated from other gases on a chromatography column and measured with a TCD.

The percent by weight of nitrogen was divided by its molecular weight of 14.0087 to determine the number of moles of nitrogen in the mixture, and that number was divided into 100 (grams) to provide the equivalent weight of 1 mole of nitrogen in the Product amine mixture as shown in Table 6, Column 4.

Table 7 thus provides the 1:1 equivalent weight reactions for the specific quantity of the amine mixture with a chloropropyltrialkoxy silane on a 1:1 equivalent basis employing the nitrogen technique. The amount of the amine mixture, according to the nitrogen technique, is reacted with the chloropropyltrialkoxy silane as shown in Table 7. The reactions were conducted in a similar fashion as reported for Operating Examples 1-13 at the reaction temperatures and reaction times reported in Table 7. The reaction mixtures were assayed for the percent of reaction completion, until 100% was achieved.

In contrast to the analytical technique of Examples 1-13, the nitrogen technique has been found to be a simplified and successful determination of the equivalent weight of one mole of the amine mixture as shown in Table 6, Column 4.

TABLE 6

(Nitrogen Technique)

| Product/Composition | Column 1 % Weight | Column 2 % Weight Nitrogen | Column 3 Mole(s) | Column 4 Equiv. Wt. 1 Mole |
|---|---|---|---|---|
| ARMEEN 18D** | | | | |
| Hexadecyl amine | 2.50% | | | |
| Octyldimethyl amine | 96.60% | | | |
| Oleyl amine | 0.50% | | | |
| Icosyl amine | 0.40% | | | |
| | 100.00% | 4.58% | 0.32694 | 305.87 |
| ADMA 18* | | | | |
| Dodecyldimethyl amine | 0.10% | | | |
| Hexadecyldimethyl amine | 1.40% | | | |
| Octadecyldimethyl amine | 98.50% | | | |
| | 100.00% | 4.53% | 0.32337 | 309.24 |
| ARMEEN DMOD** | | | | |
| Dodecyldimethyl amine | 0.50% | | | |
| Tetradecyldimethyl amine | 1.50% | | | |
| Myristoleyldimethyl amine | 0.50% | | | |
| Hexadecyldimethyl amine | 4.00% | | | |
| Palmitoleyldimethyl amine | 4.00% | | | |
| Octadecyldimethyl amine | 14.10% | | | |
| Oleyldimethyl amine | 70.40% | | | |
| Linoleyldimethyl amine | 5.00% | | | |
| | 100.00% | 4.63% | 0.330509 | 302.56 |
| CORSICANA DMOD*** | | | | |
| Hexadecyldimethyl amine | 3.00% | | | |
| Linolenicdimethyl amine | 1.00% | | | |
| Palmitoleyldimethyl amine | 6.00% | | | |
| Dimethyllinolenic amine | 1.00% | | | |
| Oleyldimethyl amine | 81.00% | | | |
| Linoleyldimethyl amine | 8.00% | | | |
| | 100.00% | 4.70% | 0.330509 | 298.51 |
| ARMEEN OD** | | | | |
| Dodecyl amine | 0.50% | | | |
| Tetradecyl amine | 1.50% | | | |
| Myristoleyl amine | 0.50% | | | |
| Hexadecyl amine | 4.00% | | | |

TABLE 6-continued (Nitrogen Technique)

| Product/Composition | Column 1 % Weight | Column 2 % Weight Nitrogen | Column 3 Mole(s) | Column 4 Equiv. Wt. 1 Mole |
|---|---|---|---|---|
| Palmitoleyl amine | 4.00% | | | |
| Octadecyl amine | 14.10% | | | |
| Oleyl amine | 71.40% | | | |
| Linoleyl amine | 5.00% | | | |
| | 100.00% | 4.52% | 0.322656 | 309.93 |
| ALBEMARLE 18D* | | | | |
| Hexadecyl amine | 2.50% | | | |
| Octadecyl amine | 96.50% | | | |
| Oleyl amine | 0.50% | | | |
| Icosyl amine | 0.40% | | | |
| | 100.00% | 4.58% | 0.32694 | 305.87 |

*ALBEMARLE AMINES
**AKSO NOBEL
***CORSICANA AMINES

TABLE 7

EXAMPLES (NITROGEN TECHNIQUE)
1:1 EQUIVALENT WEIGHT REACTIONS

| | EXAMPLE No. | | | | | |
|---|---|---|---|---|---|---|
| | 14 | 15 | 16 | 17 | 18 | 19 |
| Amine | Armeen 18D** | ADMA 18* | Armeen DMOD** | Corsicana DMOD*** | Armeen OD** | Albemarle 18D* |
| Equivalent Weight | 305.87 | 309.24 | 302.56 | 298.51 | 309.93 | 306.22 |
| Grams | 150 | 202.37 | 302.56 | 298.51 | 294.74 | 306.22 |
| Mole(s) | 0.4904 | 0.6544 | 1.000 | 1.000 | 0.951 | 1.000 |
| Chloropropyltri-alkoxysilane | KB 703 | Z-6376 | KB 703 | KB 703 | KB 703 | KB 703 |
| Equivalent Weight | 198.72 | 240.8 | 198.72 | 198.72 | 198.72 | 198.72 |
| Grams | 97.45 | 157.58 | 198.72 | 198.72 | 188.98 | 198.72 |
| Mole(s) | 0.4904 | 0.6544 | 1.000 | 1.000 | 0.951 | 1.000 |
| Available Chlorine Atoms - Wgt. % | 6.92 | 10.40 | 14.10 | 14.10 | 13.42 | 14.10 |
| Reaction Temp. (° C.) | 100° | 90° | 100° | 90° | 90°-100° | 90°-100° |
| Reaction Time (Hrs) | 21 | 48 | 19 | 48 | 35 | 120 |
| Reacted Product Assay | | | | | | |
| Titration (ppm) | 500 | 500 | 500 | 500 | 500 | 500 |
| % Complete | 100% | 100% | 100% | 100% | 100% | 100% |
| pH Hydrion Quat Chek (ppm) | 400-600 | 400-600 | 400-600 | 400-600 | 400-600 | 400-600 |
| Free Chloride Ions - Wgt. % (Calculated) | 6.92 | 10.40 | 14.10 | 14.10 | 13.42 | 14.10 |
| Form | Hard Wax | Soft Wax | Oil | Oil | Oil | Hard Wax |
| Non-Crystalline Product Performance | Yes | Yes | Yes | Yes | Yes | Yes |
| Aqueous solution @ 500 ppm | Clear | Clear | Clear | Clear | Clear | Clear |
| Barrier coating on glass surface | Yes | Yes | Yes | Yes | Yes | Yes |
| Coated glass repels ink highlighter | Yes | Yes | Yes | Yes | Yes | Yes |

*ALBEMARLE AMINES
**AKSO NOBEL
***CORSICANA AMINES

The 1:1 equivalent weight reactions of alkyl amines and chloropropyltrialkoxysilanes can also be carried out using continuous thin-film reactors at temperatures and flow rates as determine by the size and capability of the thin-film reactor employed.

Those schooled in chemical production processes will understand that the manufacture of neat silylated quaternary ammonium compounds can be scaled up with relative ease as long as the 1:1 equivalent weight ratio of the reactants is maintained and the components are mixed as is appropriate to the size/shape of the vessel(s) to ensure uniform heat exchange of the components.

Each chloropropyltrialkoxysilane molecule has a chlorine atom. When these molecules are quaternized with alkylamines, the chlorine atom is released as a free chloride ion in what is now an organosilane quaternary composition. One chloride ion is released for every molecule of silane quat that is formed. When the resulting organosilane quat composition is diluted in water, the chloride ion concentration can be measured to determine and confirm the degree of the reaction.

To confirm the complete reaction of this neat manufacturing process by either the analytical technique or the nitrogen technique, the resulting siliconized quaternary ammonium compounds were assayed by the Titrimetric Analysis Method developed by CHEMetrics, Inc., Calverton, Va. That method determines the presence of quaternary ammonium compounds in the 100 to 1000 ppm range. For the analysis, a one gram sample was removed from the neat composition and dissolved in one gram of propylene glycol. One gram of the propylene glycol/silane quat solution was dissolved in 1000 grams of pH 3 deionized water to yield a 500 ppm solution of siliconized quaternary ammonium chloride, which is equivalent to a dilution of 2000:1. Being at the mid-range of the detection capabilities of the analysis method, this proves the 100% conversion of the alkyl amines and chloropropyltrialkoxysilane to the desired neat quaternized silane composition of matter. A confirmatory test, utilizing a less sensitive pHydron Quat Check technique measuring from 0 to 1000 ppm, also proved the neat quaternized silane composition to be in the 500 ppm range.

Surprisingly, the range of amines listed herein, when reacted with chloropropyltrialkoxysilanes according to the process of this invention, yield fully reacted amorphous organosilane quats that are hard or soft waxes, oils, creams, or other solids that do not crystallize on storage, are freeze/thaw stable, and are infinitely diluteable with water and/or alcohol to make interactive surface-bondable water, soil & stain repellent coatings for hard and soft surfaces.

END USES OF THE ORGANOSILANE QUATS

The invention may be further understood by the following disclosure and end-uses of the solvent-free, storage-stable organosilane quats. The following terms have been used in this description for the purpose of describing this invention and particular embodiments.

"abrasion resistant" refers to a surface, surface coating or finish that is resistant to damage or removal by washing, scraping or scrubbing with a mildly abrasive substance or process without visibly damaging to the surface or finish, as in scratching or blemishing the surface.

"active" or "activity" means the percentage of reactive organosilane quaternary ammonium compounds including free chloride ions as manufactured, and which can be diluted into interactive compositions that will react with and bond to a surface. "100% active" means a silane quat composition that does not contain solvents, and which is essentially free of impurities such as unreacted alkylamines and chloropropylsilanes that are present in heretofore commercially available silane quats exemplified by the 42% or 72% active commercial products.

"amorphous" means having no real or apparent crystalline form.

"antimicrobial" means the elimination, reduction and/or inhibition of microorganism growth such as mold, virus, fungus or bacteria.

"bond", "bonded" or "bondable" means the ability to strongly adhere the composition to the surface, as in the ability to bond a water & soil repellent finish, coating or characteristic to an otherwise water and soil accepting surface. As used herein, the diluted composition made from an essentially 100% active compound is deemed "bonded" or "bondable" when it is resistant to removal by soaps, solvents, detergents or abrasive-type cleansers that would not otherwise stain, blemish or damage an untreated form of the same surface.

"chloride" or "free chloride ions" means a chlorine atom with a negative charge. A free chloride ion is a negatively-charged chlorine atom that can freely dis-associate from the positively-charged silane quat manufactured by the process of this invention.

"crystal" or "crystalline" means the hard, solidified form of a substance having plane faces arranged in a symmetrical, three-dimensional pattern. As used herein, "non-crystalline" or "amorphous" means a siliconized quaternary ammonium composition that, at any activity level or dilution, does not harden and solidify into such symmetrical, three-dimensional patterns or particles when cooled below 50° F. or when evaporated to dryness.

"durable" or "durability" means long-lasting and not easily removed by washing and/or wiping using plain (tap) water, soap solutions, detergent solutions, household or automotive solvents, mildly abrasive (non-damaging) cleansers or conventional cleaner/degreasers.

"easier next-time cleaning" means the extent to which surfaces cleaned and protected with water & soil repellent coatings reduce the adhesion and buildup of re-soiling and allow the re-deposited soil to be cleaned/removed with less washing, scraping and scrubbing compared to surfaces that have not been rendered water & soil repellent by the practice of this invention.

"equivalent weight" means the quantity of a substance that exactly reacts with, or is equal to the combining value, of another substance in a particular reaction, according to Encyclopedia Britannica. This definition applies to this invention, in this case the reaction of a a mixture of alkylamines and chloropropylalkoxysilanes.

"everyday surfaces" as used herein means the full range of surfaces in homes, offices, factories, public buildings and facilities, vehicles, aircraft and ships, and the like.

"household soil" means the spills, splatters and blemishes on a surface that result from cooking, eating, drinking, washing, bathing and showering such as milk, coffee, tea, juices, sauces, gravies, food boil over, soap scum, water spots, mineral deposits and tracked-in soil, etc.

"multifunctional" means the process of achieving two or more discernable results from a single application of a composition made from the essentially 100% active compound, as in simultaneously or sequentially cleaning and coating a surface whereby the coating also performs the function(s) of rendering the surface water repellent, soil repellent and/or antimicrobial.

"surface(s)" means the full range of hard or soft surfaces, rather porous or non-porous, siliceous or non-siliceous, as exemplified by everyday surfaces and such as those used in the examples which illustrate the compositions made from the compound and methods of this invention. Examples of surfaces that can be beneficially treated with compositions made from the compounds and methods of this invention include, without limitation, metal, glass, plastics, rubber, porcelain, ceramics, marble, granite, cement, tile, sand, silica, enameled appliances, polyurethane, polyester, polyacrylic, melamine/phenolic resins, polycarbonate, siliceous, painted surfaces, wood and the like.

"reaction" means the extent to which alkylamines and chloropropylalkoxysilanes react with each other to form organosilane quats as a function of the concentration of the reactants, the temperature at which the reaction is carried out, the influence of catalysts and the impact of solvents, if any.

"resistant to removal" means a coating or surface finish that is not easily removed by washing or cleaning with conventional soaps, solvents, detergents, mildly abrasive cleansers or clean/degreasers that would otherwise etch or damage an untreated surface of the same composition and construction.

"soil repellent" means a surface that exhibits reduced adhesion to, and buildup of, for example, everyday household and vehicular soil both before and after evaporation of the water and/or solvent component(s).

"solvent-free" means a free of solvent, typically an alcoholic or other solvent found in prior art products that was added to the reactants to facilitate the reaction, or to make the compound storage-stable following the reaction.

"storage-stable" refers to a useful shelf life and activity of the neat organosilanes quat compositions, or their diluted liquid compositional form, when stored in containers under ambient environmental conditions of temperature as found in warehouses, shipping containers, packages, etc., up to 120° F. for months, typically desired for more than six months or at least one year.

"vehicular soil" means the spills, splatters and blemishes on the exterior of a vehicular surface that result from rain, sleet, snow, insects, mud and road grim, and on the interior of a vehicular surface from fingerprints, food spillage, plasticizer leaching, smoking, use of hair and deodorizing sprays, dust and air circulation.

"water repellent" and "water repellency" means the hydrophobic nature or characteristic of a surface and its ability to repel water as measured by the contact angle of a drop or droplet of distilled water on the surface. (Contact angles measured with rain water, ground water or municipally furnished tap water are typically more variable and non-reproducible, and commonly measure up to 10° less than those using distilled or deionized water.) Generally, the hydrophobicity of a discrete surface is rated in terms of its contact angle to water drops as follows:

Excellent—Compact drops, well rounded, with bright sparkles measuring 95° or more.

Good—Less rounded drops, but bright sparkles that exhibit slight spread, measuring 85° to 95°.

Fair—Visible flattening of the water drops, measuring 70° to 85°.

Poor—Relatively flat water drops, exhibiting more spread of the water and measuring 50° to 70°.

To qualitatively test the end-uses of 500 ppm solutions for the ability to clean and simultaneously form water, soil & stain repellent coatings on household and vehicular abrasion resistant surfaces, soiled glass mirrors, ceramic tiles, stainless steel panels and plastic laminates were cleaned using "spray & wipe dry" application techniques. The now-cleaned surfaces were examined and found to be free of residual soil and fingerprints, and, when washed with tap water, demonstrated uniform hydrophobicity.

To determine the durability of the water, soil & stain repellent coatings that are formed when using the compositions to clean and/or treat surfaces to make them water, soil & stain repellent, glass mirrors, ceramic tiles, stainless steel panels and plastic laminates were scrubbed with Miracle Scrub, a non-scratching, mildly abrasive hard surface cleanser manufactured by Unelko Corporation, Scottsdale, Ariz., using a moist cellulose sponge. After cleansing, those everyday surfaces were rinsed with hot water to remove all cleanser residues, followed by rinsing with deionized water and drying the surfaces with paper towels. When tested with tap water droplets, each of the surfaces still exhibited fair hydrophobicity.

The tap water droplets were allowed to air dry for 24 hours, and exhibited the presence of water spots. The end-uses of 500 ppm active silane quat solutions were tested by spraying onto the surfaces and wiped dry with paper towels. The surfaces were judged to be clean (free of water spots), and, when sprayed with tap water, were observed to be hydrophobic (water repellent) in the excellent to good range as evidenced by the roundness of the water drops (high contact angle) with little spreading. When the surfaces were tilted to an incline, the water drops rolled down the surfaces. This demonstrated the presence of a hydrophobic barrier coating formed on the surface while cleaning.

The water repellent barrier coating was also confirmed by marking the surfaces with a fluorescent ink highlighter that refused to coalesce on the surface in a uniform line; instead breaking up into discrete droplets compared to the smooth, continuous line formed on an untreated surface.

A further advantage of essentially fully-reacted, solvent-free organosilane quaternaries is that they are not as pH sensitive as are conventional organosilane quaternaries. Thus, unlike conventional organosilane quaternaries which must be maintained at pH levels of 3 to 5 when compounding them into end-use products, the essentially fully-reacted, solvent-free organosilane quaternaries are stable across pH levels of about 2 to 9. This allows them to be formulated with additives like surfactants, non-reactive abrasives and quaternary ammonium compounds having alkalinity levels of up to a pH of about 9 to 10.

Those of ordinary skill in the art realize that the descriptions, procedures, methods and compositions presented above can be revised or modified without deviating from the scope of the described embodiments, and such do not depart from the scope of the invention.

What is claimed is:

1. A solvent-free, storage-stable liquid mixture of amorphous organosilane quaternary ammonium compounds derived from the reaction at a ratio of 1:1 the molecular equivalent weight of a mixture of fatty amines with the molecular equivalent weight of a chloroalkyl trialkoxysilane without a solvent to produce said liquid mixture and defined by the formula:

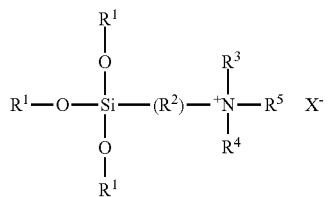

wherein $R^1$=hydrogen and/or $C_1$ to $C_4$ alkyl; $R^2$=divalent hydrocarbon radical with $C_1$ to $C_8$ carbon atoms; $R^3$=hydrogen or $C_1$ to $C_4$ alkyl; $R^4$=hydrogen or $C_1$ to $C_{10}$ alkyl; $R^5$=$C_8$ to $C_{22}$ saturated or unsaturated hydrocarbon radical and X=chloride.

2. The liquid mixture of claim 1 wherein $R^1$ is methyl or ethyl; $R^2$ is propyl; $R^3$ is methyl or hydrogen; $R^4$ is methyl or hydrogen; and $R^5$ is octyl, decyl, dodecyl, tetradecyl, tetradecenyl, hexadecyl, palmitoleyl octadecyl, oleyl, linoleyl, docosyl, or icosyl.

3. The liquid mixture of claim 1 wherein containing an organosilane quaternary ammonium compound selected from the group consisting of
   3-(trimethoxysilyl)propyldimethyloctadecyl ammonium chloride,
   3-(trimethoxysilyl)propyldimethyldecyl ammonium chloride,
   3-(trimethoxysilyl)propyldimethyldodecyl ammonium chloride,
   3-(trimethoxysilyl)propyldidecylmethyl ammonium chloride,
   3-(trimethoxysilyl)propyltetradecyldimethyl ammonium chloride,
   3-(trimethoxysilyl)propyldimethylhexadecyl ammonium chloride,
   3-(trimethoxysilyl)propyldimethylsoya ammonium chloride,
   3-(trimethoxysilyl)propyldimethyloleyl ammonium chloride,
   3-(trimethoxysilyl)propyldimethylpalmitoleyl ammonium chloride,
   3-(trimethoxysilyl)propyldimethylicosyl ammonium chloride,
   3-(trihydroxysilyl)propyldimethyloctadecyl ammonium chloride,
   3-(trimethoxysilyl)propyloctyl ammonium chloride,
   3-(trimethoxysilyl)propyldecyl ammonium chloride,
   3-(trimethoxysilyl)propyltetradecyl ammonium chloride,
   3-(trimethoxysilyl)propyltetradecenyl ammonium chloride,
   3-(trimethoxysilyl)propylhexadecyl ammonium chloride,
   3-(trimethoxysilyl)propylpalmitoleyl ammonium chloride,
   3-(trimethoxysilyl)propyloctadecyl ammonium chloride,
   3-(trimethoxysilyl)propyloleyl ammonium chloride,
   3-(trimethoxysilyl)propyldocosyl ammonium chloride,
   3-(trimethoxysilyl)propylicosyl ammonium chloride,
   3-(trimethoxysilyl)propyldimethylmyristoleyl ammonium chloride, and
   3-(trimethoxysilyl)propyldimethyldocosyl ammonium chloride, and mixtures thereof.

4. The liquid mixture of claim 1 and water wherein the liquid mixture of organosilane quaternary ammonium compounds is present in an amount of at least about 0.0002% by total weight of the liquid mixture of the compounds and water.

5. The liquid mixture of claim 4 wherein said liquid mixture of organosilane quaternary ammonium compounds is present in an amount of about 42% by total weight of the liquid mixture of the compounds and water.

6. The liquid mixture of claim 4 wherein said liquid mixture of organosilane quaternary ammonium compounds is present in an amount of about 72% by total weight of the mixture of the compounds and water.

7. The liquid mixture of claim 4 as a liquid ready-to-use product.

8. The liquid mixture of claim 7 as a storage-stable cleaning and multifunctional coating composition for treating a surface, thereby rendering it water and soil repellent.

9. The liquid mixture of claim 8 containing nonreactive abrasive solid particles.

10. The liquid mixture of claim 9 in the form of a slurry, cream, gel, or powder.

11. The liquid mixture of claim 9 wherein nonreactive abrasive particles are contained in an amount up to about 35% by weight.

12. The liquid mixture of claim 11 wherein said nonreactive abrasive particles are selected from the group consisting of coated or uncoated urea, silicas, silicates, metal oxides, metal carbonates, clays, carbides, and plastics.

13. The liquid mixture of claim 4 and water to form a liquid, slurry, cream, or powder, wherein said liquid mixture of organosilane quaternary ammonium compounds is present in a concentration at least about 0.0002% based on the total weight of said liquid mixture of compounds and water.

14. The liquid mixture of claim 13 wherein said liquid mixture of organosilane quaternary ammonium compounds is present in an effective amount for cleaning a surface and for bonding a multifunctional coating onto said surface thereby rendering it (a) water and soil repellent, (b) antimicrobial, and (c) for easier next-time cleaning.

15. The liquid mixture of claim 4 and an additive selected from the group consisting of surfactant, thickener, gelling agent, abrasive, lubricant, diluent, solvent, fragrance, colorant, peroxides, and mixtures thereof.

16. The liquid mixture of claim 4 containing hydrogen peroxide or a complex thereof.

17. The liquid mixture of claim 16 as a liquid concentrate wherein hydrogen peroxide is in an amount up to about 8% by weight, and said liquid mixture of organosilane quaternary ammonium compounds is present in an amount up to about 8% by weight.

18. The liquid mixture of claim 16 wherein said hydrogen peroxide is present in an amount up to about 3% by weight, and said liquid mixture of organosilane quaternary ammonium compounds is present in an amount of about 3% by weight.

19. A method of making a solvent-free storage-stable mixture of organosilane quaternary ammonium compounds from a mixture of fatty amines and a chloroalkyltrialkoxysilane comprising
   determining the molecular composition and equivalent weight of a mixture of fatty amines selected from the group of primary, secondary, and tertiary amines, and mixtures thereof, wherein at least one radical of said fatty amines has a linear hydrocarbon chain length ranging from a $C_8$-$C_{22}$ saturated or unsaturated hydrocarbon group,
   determining the molecular composition and equivalent weight of a chloroalkyltrialkoxysilane, and
   reacting at a ratio of 1:1 the molecular equivalent weight of said fatty amine mixture with the molecular equivalent weight of said chloroalkyltrialkoxysilane without a solvent to form a solvent-free, storage-stable mixture of organosilane quaternary ammonium compounds defined by the formula

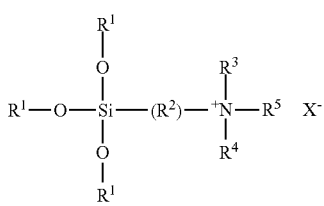

wherein $R^1$=hydrogen and/or $C_1$ to $C_4$ alkyl; $R^2$=divalent hydrocarbon radical with $C_1$ to $C_8$ carbon atoms; $R^3$=hydrogen or $C_1$ to $C_4$ alkyl; $R^4$=hydrogen or $C_1$ to $C_{10}$ alkyl; $R^5$=$C_8$ to $C_{22}$ saturated or unsaturated hydrocarbon radical and X=chloride.

20. The method of claim 19 wherein said chloroalkyltrialkoxysilane is selected from the group consisting of chloropropyltrimethoxysilane and chloropropyltriethoxysilane, and mixtures thereof.

21. The method of claim 19 wherein the molecular composition and equivalent weight of the mixture of fatty amines is obtained by identifying the relative percentage of each amine in the mixture to determine the molecular equivalent weight of the entire mixture for the 1:1 reaction with the molecular equivalent weight of the chloroalkyltrialkoxysilane.

22. The method of claim 19 wherein the molecular composition and equivalent weight of the mixture of fatty amines is obtained by identifying the percentage by weight of nitrogen in the mixture to determine the molecular equivalent weight of the entire mixture for the 1:1 reaction with the molecular equivalent weight of the chloroalkyltrialkoxysilane.

23. The method of claim 19 wherein said mixture of fatty amines is selected from the group consisting of
octyldimethyl amine,
decyldimethyl amine,
dodecyldimethyl amine,
tetradecyldimethyl amine,
hexadecyldimethyl amine,
octadecyldimethyl amine,
palmitoleyldimethyl amine,
oleyldimethyl amine,
icosyldimethyl amine,
myristoleyldimethyl amine,
dodecyl amine,
tetradecyl amine,
myristoleyl amine,
hexadecyl amine,
palmitoleyl amine,
octadecyl amine,
oleyl amine,
icosyl amine,
docosyl amine,
octyl amine, and
decyl amine, and mixtures thereof.

24. The method of claim 23 wherein said chloroalkyltrialkoxysilane is selected from the group consisting of chloropropyltrimethoxysilane and chloropropyltriethoxysilane, and mixtures thereof.

25. The method of claim 19 conducted at a temperature of about 20° C. to about 120° C.

* * * * *